United States Patent [19]
Tanaka et al.

[11] Patent Number: 6,019,989
[45] Date of Patent: Feb. 1, 2000

[54] SKIN ACTIVATOR WITH GLYCOSAMINOGLYCAN PRODUCTION-ACCELERATING EFFECT

[75] Inventors: Shinji Tanaka, Tsukuba; Hiroshi Doi, Tsuchiura; Noboru Yamamoto, Sagamihara, all of Japan

[73] Assignee: Institute for Advanced Skin Research Inc., Kanagawa, Japan

[21] Appl. No.: 08/600,941

[22] PCT Filed: Jun. 21, 1995

[86] PCT No.: PCT/JP95/01244

§ 371 Date: Feb. 21, 1996

§ 102(e) Date: Feb. 21, 1996

[87] PCT Pub. No.: WO95/35091

PCT Pub. Date: Dec. 28, 1995

[30] Foreign Application Priority Data

Jun. 21, 1994 [JP] Japan .................................. 6-138637

[51] Int. Cl.⁷ ...................................................... A61K 6/00
[52] U.S. Cl. ........................... 424/401; 424/450; 514/785
[58] Field of Search .............................. 514/77, 114, 785; 424/401, 450

[56] References Cited

U.S. PATENT DOCUMENTS 4,104,403  8/1978  Barker et al. ............................ 424/365
4,370,319  1/1983  Chapin et al. ........................... 424/184

FOREIGN PATENT DOCUMENTS 2-138132  5/1990  Japan .
3-66604   3/1991  Japan .
5-271049  10/1993 Japan .
9221323   12/1992 WIPO .

OTHER PUBLICATIONS

Van Corven et al., Mitogenic Action of Lysophosphatidic Acid and Phosphatidic Acid on Fibroblasts. Dependence on Acyl–chain Length and Inhibition by Suramin, Biochem. J. (1992) 281 (1), 163–9.

W. Moolenaar, "LPA: A Novel Lipid Mediator With Diverse Biological Actions," Trends In Cell Biology, vol. 4, Jun. 1994, pp. 213–219.

*Primary Examiner*—Jose' G. Dees
*Assistant Examiner*—Michael A. Williamson
*Attorney, Agent, or Firm*—Burns, Doane, Swecker & Mathis, L.L.P.

[57] ABSTRACT

A skin activator containing as an effective component a compound represented by the following general formula (I), and external skin preparations containing it. It has an excellent glycosaminoglycan production-accelerating effect.

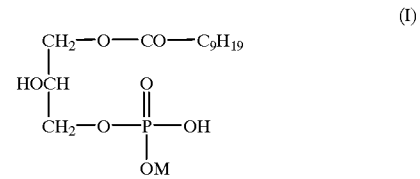

(I)

5 Claims, No Drawings

SKIN ACTIVATOR WITH GLYCOSAMINOGLYCAN PRODUCTION-ACCELERATING EFFECT

TECHNICAL FIELD

The present invention relates to a skin activator with a glycosaminoglycan production-accelerating effect, containing 1-acyl-lysophospholipid derivative as an effective component. The skin activator is useful as a cosmetic and an external preparation to prevent skin aging.

BACKGROUND ART

Primary phenomena associated with skin aging include a reduction in "moisture" and "elasticity", and the resulting wrinkles and "sagging". While the causes for this are not yet completely understood, it has been reported in J. Soc. Cosmet. Chem. Japan, 15, 77 (1981), Cell Structure and Function, 9, 357 (1984), Maria, et al., Carbohydrate Research, 159, 127–136 (1987) and elsewhere that one cause is believed to be an age-related decline in the production by skin cells of glycosaminoglycans such as hyaluronic acid, leading to a decrease in the moisture content of the skin which affects skin function. Based on this understanding, and in tandem with methods of forming an oily film on the skin surface for the purpose of passively preventing loss of moisture from the cuticle by perspiration, attention has been focused on the water retention properties of glycosaminoglycans, as a result of which hyaluronic acid derived from cockscombs and Streptococcus bacteria fermentation has been formulated into a variety of cosmetics for supplementation of a hydrophilic component, as a means of preventing wrinkles and "sagging"; however, since the hyaluronic acid in these cosmetics is simply applied onto the skin surface, the macromolecular hyaluronic acid is not absorbed into the skin and thus exhibits only a water-retention effect due to its hygroscopicity. The effect, then, is lost after washing, resulting in no substantial improvement in skin function. The only disclosed substance which activates skin cell function on the cellular level and enhances the production of glycosaminoglycans as water-retention components is egg enzymolysate, with its fractional components (Japanese Unexamined Patent Publication No. 5-271049).

Simple lysophospholipids, on the other hand, form extremely fine micelles in water due to their single-stranded structure, and thus yield fine emulsions in emulsified systems. They are characterized by having the effect of stabilizing emulsions and preventing starch aging (phenomenon of hardening and emergence due to recrystallization of starch molecules), and are thus used as emulsifiers and as modifiers for bread and the like. According to reports by Uchida, et al. (The Journal of Dermatology, 18, 523–527 (1991)), it has been demonstrated that lysophosphatidylcholine penetrates to the interior of the skin when applied to the skin surface of hairless rats without causing histological damage, and is thus highly safe as a cosmetic. This has led to the development of external skin preparations taking advantage of the safety, low irritancy and stable emulsifying effect of lysophospholipids (Japanese Unexamined Patent Publication No. 63-41411), but without dealing with their anti-aging effect on skin. Another example is Japanese Unexamined Patent Publication No. 3-161414 wherein lysophosphatidyl glycerol is formulated into a cosmetic for its water-retention effect; however, as in the case where hygroscopic hyaluronic acid is applied onto the skin surface, no effect can be expected once it is washed off.

DISCLOSURE OF THE INVENTION

Based on these results, cell activators which increase the amount of water-retaining glycosaminoglycans in the skin have been found to be effective for activating the skin from the inside, to prevent age-related morphological changes in the skin, typically a reduction in "moisture" and "elasticity" and resulting wrinkles. Nevertheless, it has been desired to develop skin beautifiers with higher glycosaminoglycan-producing ability than the effective components in the skin cosmetics described above. It is, therefore, an object of the present invention to provide a skin activator with a strong glycosaminoglycan production-accelerating effect.

As a result of continuous diligent searching for a glycosaminoglycan production-accelerating substance capable of dealing with the aforementioned problems, the present inventors have discovered that certain lysophospholipids have a notable glycosaminoglycan production-accelerating effect and are highly safe compounds, and upon this basis the present invention has been completed.

In other words, the present invention provides a skin activator containing as an effective component a compound represented by the following general formula (I):

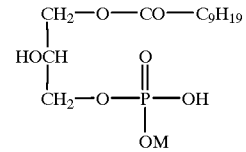

wherein M is hydrogen or an alkali metal atom.

BEST MODE FOR CARRYING OUT THE INVENTION

The compounds of general formula (I) shown above may be commercially obtained, or they may be obtained by treating the commercially available 1-decanoyl-2-acyl-lysophosphatidic acid with phospholipase A2. Alternatively, the above-mentioned compounds may also be obtained by treating synthesized 1-decanoyl-2-acyl-lysophosphatidic acid with phospholipase A2.

The skin activator of the present invention which has a glycosaminoglycan production-accelerating effect may be used as an anti-aging cosmetic for the purpose of preventing wrinkles. To obtain the glycosaminoglycan production-accelerating effect of the invention for the use described above, the mixing ratio of the compound is preferably 0.1 to 10 wt % with respect to the total external skin preparation or formulation. If the amount is less than 0.1 wt %, the desired glycosaminoglycan production acceleration will not be adequately displayed, while if it exceeds much more than 10 wt %, problems such as stickiness will result, and thus neither case is practical.

The form of the cosmetic containing the skin activator of the present invention is not particularly limited, and it may contain, in addition to the aforementioned compound as the effective component, any of a variety of cosmetic components and additives commonly used in cosmetics, including inorganic pigments, organic pigments, inorganic powders, organic powders, hydrocarbons, silicones, esters, triglycerides, lanolins, waxes, cere, animal or vegetable oils, surfactants, polyhydric alcohols, sugars, vitamins, amino acids, antioxidants, preservatives, fragrances, thickeners, and the like.

The present invention is explained in more detail by way of the following examples which, however, are in no way intended to restrict its scope.

EXAMPLES

First, we present the results of experiments conducted to evaluate the effect of the compounds of general formula (I) used according to the invention.

Evaluation of glycosaminoglycan production by NB1RGB cells

The cells used to evaluate the glycosaminoglycan production acceleration were of the human neonatal dermatofibroblast cell line NB1RGB. This cell line is often conventionally used for such experiments, and was suitable as cells for this experiment. In addition, since human derived cells were used in this experiment, they were even more appropriate as a method of evaluating a drug intended for application to the human body.

NB1RGB cells were densely seeded onto a 1.2 cm-diameter culturing dish (48 wells) at $5 \times 10^4$ per dish, and cultured for 24 hours at 37° C. in a Dulbecco's modified eagle medium containing 10% fetal calf serum. The test compound was then added to Dulbecco's modified eagle medium containing 0.5% fetal calf serum, to a concentration in the medium of 0.5 to 100 μM. After culturing for 24 hours, the cells were transferred to fresh 0.5% calf serum-containing medium to which the test compound had been added to the same concentration. $^3$H-glycosamine was also added to the medium at this time to 370 KBq/ml, and the culturing was continued for another 24 hours. After completion of the culturing, 2 mg pronase in 0.1 M Tris•HCl (pH 8) was added, and incubation was performed at 50° C. for one hour. Cetylpyridium chloride was added to a final concentration of 1% in the copresence of 100 μg hyaluronic acid as a carrier, and the resulting precipitate was separated out by centrifuge. The precipitate was centrifuged and washed 3 times in 1 ml of a 1% aqueous cetylpyridium chloride solution, and then 0.2 ml of a 0.05% aqueous cetylpyridium chloride solution containing 0.5 M NaCl was added and the mixture was vigorously stirred. To this was then added 5 ml of the emulsification scintillator ACSII, and the radiation was counted with a liquid scintillation counter, making the evaluation based on standard control values. The results, along with the Comparative Examples for contrast, are given in Table 1 below.

TABLE 1

| | Glycosaminoglycan production (ratio to control) | | | |
| --- | --- | --- | --- | --- |
| | Examples | Comparative Examples | | |
| Concentration | Compound 1 | Comp. 1 | Comp. 2 | Comp. 3 |
| 0 μM | 1 | 1 | 1 | 1 |
| 5 | 1.5 | 1 | 1.2 | 1 |
| 10 | 2 | | | |
| 50 | | | | 2.4 |
| 100 | 5 | 1 | 1 | 1.5 |

Compound 1: 1-decanoyl-lysophosphatidic acid
Comparison 1: 1-decanoyl-lysophosphatidylcholine
Comparison 2: Lysophosphatidyl glycerol
Comparison 3: Soybean phospholipid-derived lysophosphatidic-acid The following are formulation examples of skin activator-containing cosmetics according to the invention.

Example 1
(ointment 1)

| | | Parts by weight |
| --- | --- | --- |
| A | 1-decanoyl-lysophosphatidic acid | 1 |
| | White vaseline | 25 |
| | Stearyl-alcohol | 22 |
| B | Propylene glycol | 12 |
| | Sodium lauryl sulfate | 1.5 |
| | Preservative/antioxidant | q.s. |
| | Fragrance | q.s. |
| | Purified water | remainder |
| | Total | 100 |

The components listed under A were dissolved in a hot water bath (oil phase), while the components listed under B were separately heated to dissolution (aqueous phase). The aqueous phase was added to and mixed with the oil phase, and after emulsification the mixture was cooled to obtain an ointment.

Example 2
(ointment 2)

| | | Parts by weight |
| --- | --- | --- |
| A | 1-decanoyl-lysophosphatidic acid | 2 |
| | White vaseline | 40 |
| | Cetanol | 18 |
| | Sorbitan sesquioleate | 5 |
| | Lauromacrogol | 0.5 |
| B | Preservative/antioxidant | q.s. |
| | Fragrance | q.s. |
| | Purified water | remainder |
| | Total | 100 |

The components listed under A were dissolved in a hot water bath (oil phase), while the components listed under B were separately heated to dissolution (aqueous phase). The aqueous phase was added to and mixed with the oil phase, and after emulsification the mixture was cooled to obtain an ointment.

Example 3
(Neutralizing cream)

| | Parts by weight |
| --- | --- |
| 1-decanoyl-lysophosphatidic acid | 2 |
| Stearyl alcohol | 7 |
| Stearic acid | 2 |
| Hydrogenated lanolin | 2 |
| Squalene | 5 |
| 2-octyldodecyl alcohol | 6 |
| POE (25) cetyl alcohol ester | 3 |
| Glycerine monostearate ester | 2 |
| Propylene glycol | 5 |
| Preservative/antioxidant | q.s. |
| Fragrance | q.s. |
| Purified water | remainder |
| Total | 100 |

The propylene glycol was added to the purified water, heated and kept at 70° C. (aqueous phase). The other components were combined, heated to dissolution and kept at 70° C. (oil phase). The oil phase was added to the aqueous phase, and after pre-emulsification, homogeneous emulsification was performed with a homomixer to obtain a neutralizing cream.

Example 4
(emulsion)

|   |   | Parts by weight |
|---|---|---|
| A | 1-decanoyl-lysophosphatidic acid | 0.5 |
|   | Silicone KF56 | 2 |
|   | Isopropyl myristate | 3 |
|   | POE (20) POP (4) cetyl ether | 1 |
| B | Glycerin | 3 |
|   | Hibiswaco 105 | 0.2 |
|   | Preservative/antioxidant | q.s. |
|   | Fragrance | q.s. |
|   | Purified water | remainder |
|   | Total | 100 |

The above-mentioned formulas A and B were each liquefied at 70° C., A was added to B, and the mixture was homogeneously emulsified to obtain an emulsion.

Example 5
(Skin pack)

|   | Parts by weight |
|---|---|
| 1-decanoyl-lysophosphatidic acid | 3 |
| Ethyl alcohol | 10 |
| Glycerin | 5 |
| Dipropylene glycol | 5 |
| Polyethylene glycol 4000 | 1 |
| Polyvinyl alcohol | 10 |
| Vinyl acetate resin emulsion | 13 |
| Titanium oxide | 12 |
| Olive oil | 3 |
| Squalene | 0.5 |
| Preservative/antioxidant | q.s. |
| Fragrance | q.s. |
| Purified water | remainder |
| Total | 100 |

The components were uniformly dissolved to obtain a skin pack.

Example 6
(beauty wash)

|   | Parts by weight |
|---|---|
| 1-decanoyl-lysophosphatidic acid | 0.5 |
| Glycerine | 4 |
| 1,3-butylene glycol | 4 |
| Ethanol | 7 |
| POE (25) oleyl alcohol | 0.5 |
| Preservative/antioxidant | q.s. |
| Fragrance | q.s. |
| Purified water | remainder |
| Total | 100 |

The glycerine and 1,3-butylene glycol were dissolved in the purified water. Separately, the 1-decanoyl-lysophosphatidic acid and POE (20) oleyl alcohol were dissolved in the ethanol, and this solution was then added to and dissolved in the previous aqueous solution and filtered to obtain a beauty wash.

INDUSTRIAL APPLICABILITY

As mentioned above, the present invention provides a novel and remarkable glycosaminoglycan production-accelerating substance, and skin activating external preparations containing the compound as an effective component thereof display an excellent skin-beautifying effect.

We claim:

1. An external skin preparation comprising a skin activator with a glycosaminoglycan production-accelerating effect, in an amount of 0.1–10 weight % of a 1-acyl-lysophospholipid derivative represented by the following general formula (I):

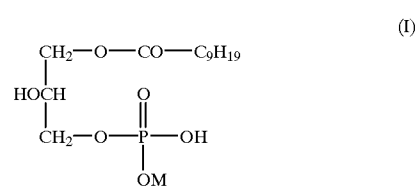

wherein M is hydrogen or an alkali metal atom.

2. An external anti-aging skin preparation comprising a skin activator with a glycosaminoglycan production-accelerating effect in an amount of 0.1–10 weight % of a 1-acyl-lysophospholipid derivative represented by the following general formula (I):

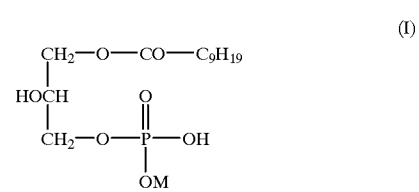

wherein M is hydrogen or an alkali metal atom.

3. A method of increasing the amount of water-retaining glycosaminoglycans in the skin comprising administering to the skin a skin activator with a glycosaminoglycan production-accelerating effect in an amount of 0.1–10 weight % of a 1-acyl-lysophospholipid derivative represented by the following general formula (I):

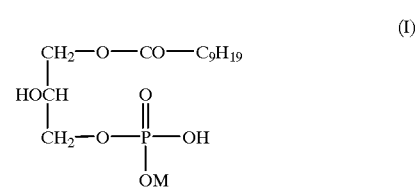

wherein M is hydrogen or an alkali metal atom for increasing the amount of water-retaining glycosaminoglycans in the skin.

4. A cosmetic composition comprising a skin activator with a glycosaminoglycan production-accelerating effect in an amount of 0.1–10 weight % of a 1-acyl-lysophospholipid derivative represented by the following general formula (I):

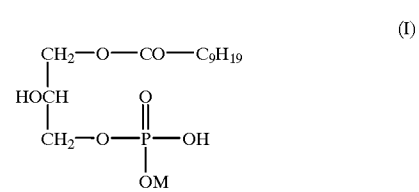

wherein M is hydrogen or an alkali metal atom for increasing the amount of water-retaining glycosaminoglycans in the skin.

5. The cosmetic composition according to claim 4 further comprising an inorganic pigment, organic pigment, inorganic powder, organic powder, hydrocarbon, silicone, ester, triglyceride, lanolin, wax, cere, animal or vegetable oil, surfactant, polyhydric alcohol, sugar, vitamin, amino acid, antioxidant, preservative, fragrance, or thickener.

* * * * *